United States Patent [19]

Symbas et al.

[11] Patent Number: 4,627,421
[45] Date of Patent: Dec. 9, 1986

[54] STERNAL RETRACTOR

[76] Inventors: Panagiotis N. Symbas, 3661 Cloudland Dr., Atlanta, Ga. 30327; J. Lee Baisden, 5010 Timber Lookout, San Antonio, Tex. 78250; Stothe P. Kezios, 1060 Winding Creek Trail, N.W., Atlanta, Ga. 30327

[21] Appl. No.: 637,419

[22] Filed: Aug. 3, 1984

[51] Int. Cl.$^4$ ............................................. A61B 17/02
[52] U.S. Cl. ................................................. 128/20
[58] Field of Search ............... 128/20, 6, 11, 13, 16, 128/18

[56] References Cited

U.S. PATENT DOCUMENTS

| | | | |
|---|---|---|---|
| 1,311,313 | 7/1919 | Brix | 128/20 |
| 1,706,500 | 3/1929 | Smith | 128/20 |
| 2,670,731 | 3/1954 | Zoll et al. | 128/20 |
| 3,626,471 | 12/1971 | Florin | 128/20 |
| 3,710,783 | 1/1973 | Jascalevich | 128/20 |
| 3,749,088 | 7/1973 | Kohlmann | 128/20 |
| 3,853,120 | 12/1974 | Batista | 128/20 |
| 3,965,890 | 6/1976 | Gauthier | 128/20 |
| 4,116,232 | 8/1978 | Rabban | 128/20 |
| 4,122,844 | 10/1978 | Rabban | 128/20 |
| 4,151,838 | 5/1979 | Crew | 128/20 |
| 4,226,228 | 10/1980 | Shin | 128/20 |
| 4,263,899 | 4/1981 | Burgin | 128/18 |
| 4,337,763 | 7/1982 | Patrassevich | 128/20 |

OTHER PUBLICATIONS

Sklar Products Surgical Instrument Catalogue, p. 220.

Primary Examiner—William H. Grieb
Attorney, Agent, or Firm—Cox & Smith Inc.

[57] ABSTRACT

A retractor with pivoting arms which reduces the amount of pressure exerted on the small ribs of the upper part of the rib cage when the rib cage is retracted for open heart surgery. One of the arms is pivotally mounted to the cross-bar and the other is pivotally mounted to a cursor. The cursor moves along the cross-bar such that as the cursor is moved along the cross-bar, the opening will be retracted in a triangular shape. Pressure is exerted evenly along the edges of the incision and the triangular configuration of the opening reduces the breakage of the small ribs of the rib cage.

10 Claims, 6 Drawing Figures

STERNAL RETRACTOR

BACKGROUND OF THE INVENTION

Open heart surgery has become one of the most common surgical procedures performed in the United States. During the process of opening the chest cavity to perform the surgery, a vertical incision is made through the skin over the breast bone (sternum) and the breast bone is then cut vertically with a surgical saw. The surgeon then gains access to the pericardial area by spreading the cut edges of the bone with a sternal retractor.

The spreading of the rib cage with the sternal retractor places great pressure on the ribs, and when the pressure becomes too great, the ribs can break. The shorter ribs, with their smaller radius, are more likely to break than the longer ribs in the middle or lower area of the rib cage. In addition to the pain caused by the broken ribs in the chest wall area after surgery, the ribs tend to break in an area in which the broken ends of the bone exert pressure against, or impale, the nerves which innervate the arms as they leave the spinal column. In approximately five to ten percent of open heart patients, these nerves are damaged by the retraction of the rib cage.

It has been suggested that the sternal retractor be placed in the cut so as to bear only against the lower two-thirds of the breast bone, thus placing less stress on the smaller, upper ribs. Placement of the retractor on the lower portion of the sternum does result in fewer broken ribs, but it places uneven pressure on the sternum itself, often resulting in breakage of the sternum. The breakage of the sternum causes increased blood loss during the surgery and presents complications because the sternum occasionally does not heal properly, often necessitating another operation at a later date.

There are a number of retractors available that are presently in use as sternal retractors. The Codman retractor consists of a cross-bar with two arms attached, one of which can be ratcheted along the length of the cross-bar to retract the rib cage. The arms are provided with detachable blades hooked to the arms by hooks which project down into the incision. The Cooley and Ankeney retractors are similar in that they also consist of cross-bars and arms, one or more of which is ratcheted along the cross-bar to retract the incision. They differ from each other, and from the Codman retractor, in the configuration of the blades which contact the incision, bearing against the sternum to retract the rib cage. The Burford-Finochietto rib spreader is provided with two arms which are racheted along the cross-bar and interchangable blades for contacting the sternum. The Finochietto rib spreader is similar but with only one movable arm. The Lemmon sternal spreader is provided with one arm which can be ratcheted along the cross-bar and the blades are modified to better retain the edges of the sternum while the rib cage is being retracted.

However, all of these prior art retractors open the rib cage in a more or less rectangular manner (i.e., they move the cut edges of the sternum away from each other while keeping them parallel to each other). The rectangular shape of the opening causes the uneven pressure on the ribs because the rib cage is not rectangularly shaped, and the result is the breakage of the smaller ribs. There is, therefore, a need for a retractor which distributes even pressure along the edges of the breast bone without exerting a great amount of pressure on the smaller ribs at the top of the rib cage.

It is an object of the present invention to provide a sternal retractor which is capable of distributing the force exerted on the rib cage evenly along the length of the incision. Another object of the present invention is to provide a sternal retractor which can be used to retract the rib cage without breaking the ribs. Another object of the present invention is to provide a retractor capable of retracting the rib cage in a triangularly-shaped opening.

Another object of the present invention is to provide a sternal retractor with pivoting arms, at least one of which can be moved along a cross-bar so as to retract the rib cage. Another object of the present invention is to reduce the damage to the nerve tissue caused by the broken ends of the ribs which may be broken during retraction of the rib cage for open heart surgery.

SUMMARY OF THE INVENTION

These objects are achieved in the present invention by providing an apparatus for spreading the walls of an opening in the body comprising a cross-bar, two elongate arms, each of which has a free end and an end pivotally mounted to the cross-bar, means for moving the pivoting end of one of the arms laterally along the cross-bar and means mounted on the arms to engage the walls of the opening.

BRIEF DESCRIPTION OF THE DRAWINGS

FIG. 2a showing a sectional view of the apparatus in its unretracted position and FIG. 2b showing a sectional view of the apparatus as it appears once the opening has been retracted.

DETAILED DESCRIPTION OF THE INVENTION

Figure 4:
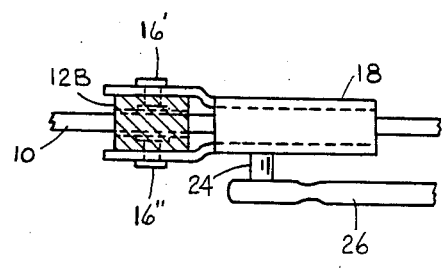
FIG. 4 is a sectional view taken along the line 4—4 in FIG. 1, with some parts shown broken away.
Figure 5:
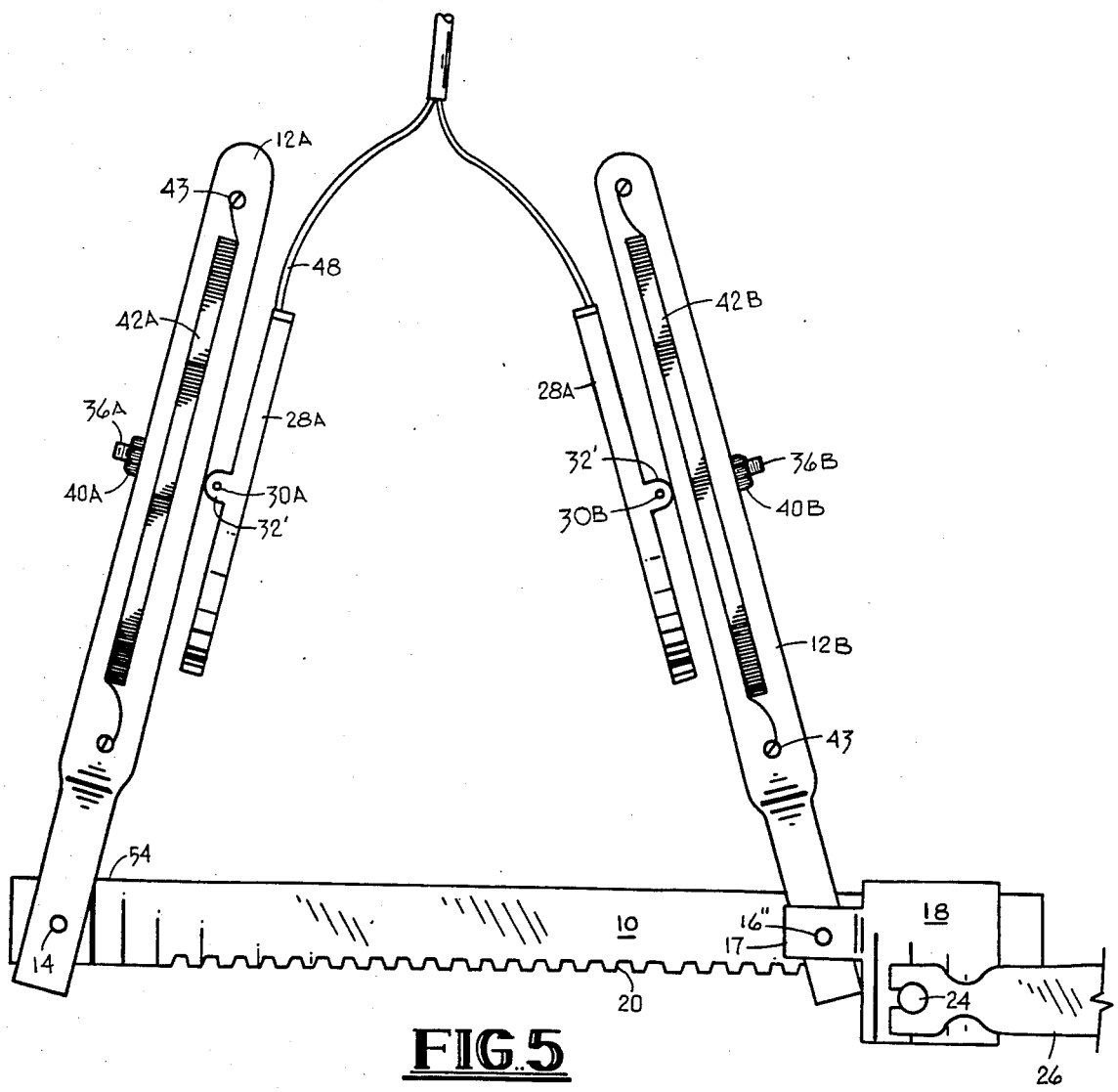
FIG. 5 is a plan view of the entire retractor as it appears in its retracted position.

Referring to FIGS. 1, 2a and 2b, and 5, there is shown a cross-bar 10 to which a pair of pivoting arms 12a and 12b are mounted. Pivoting arm 12a is mounted to cross-bar 10 on pin 14. Arm 12b is mounted on pins 16' and 16" to the extension 17 of movable member 18 (see FIG. 4). In a presently preferred embodiment, the arms 12a and 12b are tapered toward their free ends and curved slightly downwardly. Movable member 18 is moved along cross-bar 10 by means of the engagement of rack 20 on the cross-bar 10 by pinion 22 which is integral with axle 24. Axle 24 is rotated by means of integral handle 26.

Figure 1:
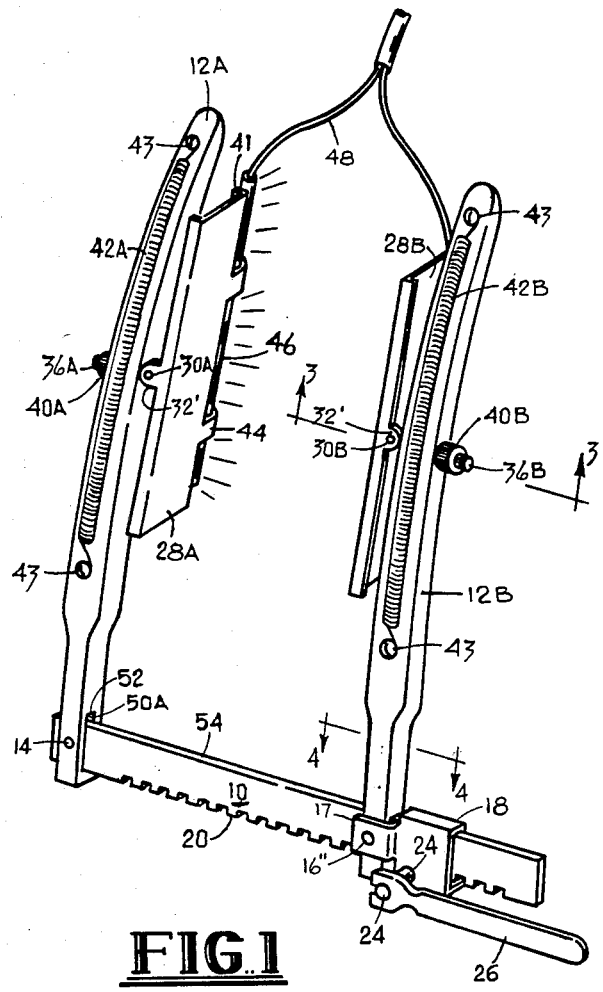
FIG. 1 is a plan view of a preferred embodiment of the present invention.
Figure 2A:
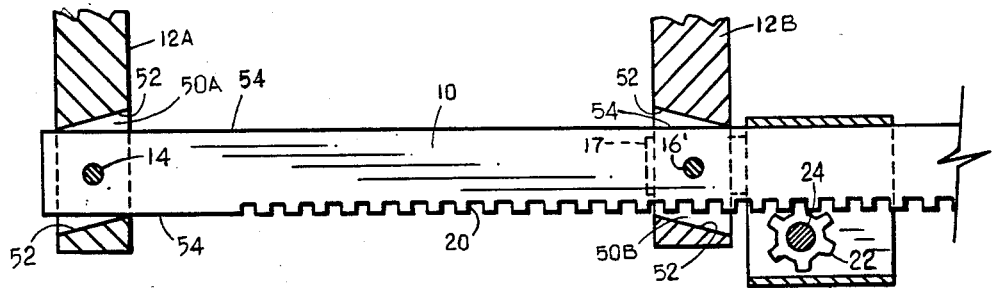
FIGS. 2a and 2b are longitudinal cross sections through the cross-bar of the apparatus shown in FIG. 1, the arms of the apparatus being broken away.
Figure 2B:
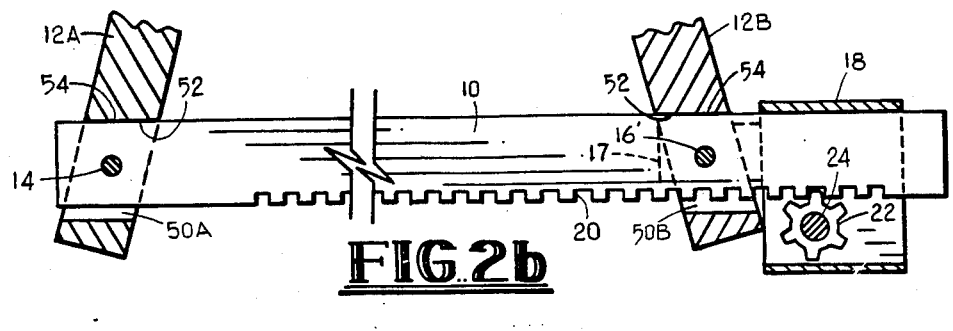
Figure 3:
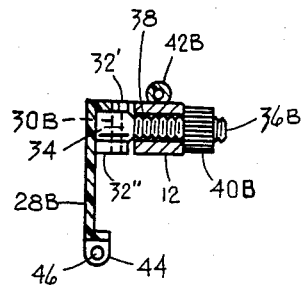
FIG. 3 is a sectional view taken along the line 3—3 in FIG. 1.

Each of the arms 12a and 12b are provided with blades 28a and 28b. Blades 28a and 28b are pivotally mounted on cotter pins 30a and 30b (shown in shadow lines in FIG. 3) which engage the ears 32' and 32". The cotter pins 30a and 30b are free to rotate within the head 34 of screws 36a and 36b (see FIG. 3). Screws 36a and 36b pass through bores 38a and 38b in arms 12a and 12b, respectively, and are free to rotate within the bores 38a and 38b. Screws 36a and 36b are held in place by nuts 40a and 40b. This arrangement of cotter pins 30, screws 36 and bores 28 allows the blades to pivot in two planes to help them retain their position along the edges of the incision even if, during retraction of the rib cage, one of the edges change in height or alignment relative to the other edge. The blades 28a and 28b can pivot in the same plane in which the arms 12a and 12b and cross-bar 10 lie as well as in a plane parallel with arms 12a and 12b but perpendicular to the plane of the cross-bar 10. Nuts 40a and 40b can be hand tightened to position the blades 28a and 28b to help hold the edges of the incision in a particular alignment once the rib cage has been retracted. Blades 28a and 28b are provided with a lip 41 to keep the blade from slipping off of the cut edge of the breast bone as the rib cage is retracted.

In a preferred embodiment of the present invention, arms 12a and 12b are provided with coil springs 42a and 42b held in place by screws 43 so that the surgeon performing the surgery can use the coils of the spring to retain the loose ends of the sutures with which he is working in the opening created by the retractor. The blades 28a and 28b are provided with stays 44 to retain the light source 46, which may be a fiber optic cord 48 which is modified within the area 46 to provide light in the desired direction to illuminate the area down inside the incision.

Arms 12a and 12b are provided with channels 50a and 50b. The edges 52 of the channels 50a and 50b are angled at an angle of about between 5 and about 60 degrees, the angle of a presently preferred embodiment being approximately 15 degrees, from the horizontal edges 54 of the cross-bar 10 when the arms are perpendicular to the cross-bar. In this manner, the arm 12a is free to pivot on the pin 14 and the arm 12b is free to pivot on pins 16' and 16". Because of the angle of the edges 52 of channels 50a and 50b, the free ends of each arm 12a and 12b can pivot only inwardly towards each other. In the preferred embodiment, each of the arms can pivot to a point at which it is approximately 15 degrees away from being perpendicular to the cross-bar 10.

To use the apparatus of the present invention, after an incision is made in the breast bone, the blades 28a and 28b are inserted into the incision at approximately the mid-point of the sternum. The handle 26 is then used to move the movable member 18, carrying the arm 12b along with it, across the cross-bar 10. As the movable member 18 carries the arm 12b along the cross-bar 10 in a direction away from the pin 14, the arm 12a and 12b start to pivot such that the free end of the arms are carried inwardly towards each other. The arms 12a and 12b pivot until the edges 52 of the channels 50a and 50b contact the horizontal edges 54 of the cross-bar 10. Once the edges 52 and 54 have contacted, the arms 12a and 12b can pivot no further, and the continued movement of the arm 12b along the cross-bar 10 causes the retraction of the rib cage. The blades 28a and 28b can simultaneously pivot in two directions so as to be able to firmly engage the edges of the incision in spite of any nonlinearity in the edges of the opening or changes in the alignment of the edges. In this manner, a triangular opening is created, decreasing the stress applied to the smaller ribs of the upper part of the rib cage.

Although the present invention has been described with reference to a preferred embodiment, it will be recognized by those of ordinary skill in the art who have the benefit of this disclosure that a number of modifications may be made to it. It is expected that such modifications will fall within the spirit and scope of the following claims.

What is claimed is:

1. Apparatus for spreading the walls of an opening in the body of a human or other animal comprising:
   a cross-bar;
   two elongate arms, each of said arms having a free end and an end pivotally mounted to said cross-bar;
   means for moving the pivoting end of one of said arms laterally along said cross-bar; and
   means mounted on each of said arms for engaging the walls of an opening.

2. The apparatus of claim 1 wherein said lateral arm moving means is a cursor movable along the length of said cross-bar, one of said arms being pivotally mounted to said cursor.

3. The apparatus of claim 2 wherein said cursor is moved along the length of said cross-bar by rotation of a pinion, said pinion engaging a rack on said cross-bar.

4. The apparatus of claim 1 wherein said wall engaging means is pivotally mounted to said arms.

5. The apparatus of claim 1 wherein said wall engaging means is pivotally mounted to said arms to allow pivoting of said wall engaging means in a plane substantially parallel to the plane of both said cross-bar and said arms and to simultaneously allow pivoting of said wall engaging means in a plane substantially perpendicular to said cross-bar and parallel to said arms.

6. The apparatus of claim 1 wherein said arms are provided with elongate coil springs.

7. The apparatus of claim 1 wherein said wall engaging means is provided with an elongate light source.

8. The apparatus of claim 7 wherein said light source comprises an optic fiber, the end of which is modified to illuminate the area between the walls of the opening.

9. The apparatus of claim 1 wherein said arms pivot to a point at which they are between approximately 5 and approximately 60 degrees from being perpendicular to said cross-bar.

10. The apparatus of claim 1 wherein said arms pivot to a point at which they are approximately 15 degrees from being perpendicular to said cross-bar.

* * * * *